United States Patent [19]

Ogle, II

[11] Patent Number: 4,979,941

[45] Date of Patent: Dec. 25, 1990

[54] DEVICE SUITABLE FOR MIXING MEDICATION

[75] Inventor: George B. Ogle, II, Alta Loma, Calif.

[73] Assignee: International Medication Systems, Limited, South El Monte, Calif.

[21] Appl. No.: 446,396

[22] Filed: Dec. 5, 1989

[51] Int. Cl.$^5$ .......... A61M 37/00

[52] U.S. Cl. .......... 604/82; 222/83; 604/89; 604/411; 604/414

[58] Field of Search .......... 604/82, 87-89, 604/91, 191, 411, 413, 414-416, 905; 222/83, 83.5, 85, 129, 145, 160, 162

[56] References Cited

U.S. PATENT DOCUMENTS

| | | | |
|---|---|---|---|
| 3,563,415 | 2/1971 | Ogle | 222/145 |
| 3,603,484 | 9/1971 | Ogle | 222/94 |
| 3,670,728 | 6/1972 | Dabney | 604/91 |
| 3,674,028 | 7/1972 | Ogle | 128/272 |
| 3,802,604 | 4/1974 | Morane et al. | 222/83 |
| 3,842,836 | 10/1974 | Ogle | 128/272 |
| 3,857,392 | 12/1974 | Ogle | 128/214 C |
| 3,858,580 | 1/1975 | Ogle | 128/214 C |
| 3,882,909 | 5/1975 | Ogle | 141/286 |
| 3,941,171 | 3/1976 | Ogle | 141/309 |
| 4,392,850 | 7/1983 | Elias et al. | 604/82 |
| 4,559,983 | 12/1985 | Paoletti | 141/260 |
| 4,610,374 | 9/1986 | Buehler | 222/83 |
| 4,871,354 | 10/1989 | Conn et al. | 604/89 |

*Primary Examiner*—C. Fred Rosenbaum
*Assistant Examiner*—C. Maglione
*Attorney, Agent, or Firm*—Christie, Parker & Hale

[57] ABSTRACT

The present invention comprises a device suitable for mixing medicaments which comprises two separate containers. The first container is provided with a reservoir section and a neck section such that the cross section of the neck section is less than the cross section of the reservoir. A stopper is snugly fit within the neck section adjacent to the reservoir and a spike and plunger member is snugly fit within the neck section adjacent the stopper on the side opposite the reservoir. The spike and plunger member has a midportion with a hole therein, and a plunger projecting from the midportion adapted to make contact with the stopper. A spike extends from the midportion in the opposite direction.

5 Claims, 2 Drawing Sheets

DEVICE SUITABLE FOR MIXING MEDICATION

BACKGROUND OF THE INVENTION

It is often necessary to mix powder and/or liquid medicaments before dispensing the mixture either by syringe or other means. In such cases, it is desirable to effect the preparation of the mixture just prior to the need to dispense the same. Moreover, many medicaments must be prepared, stored, and supplied in a dry or lyophilized form, and must be reconstituted at time of use by addition of a diluent thereto.

A variety of methods have been proposed for adding the diluents to the dry or lyophilized medicament. So-called "open-pour techniques" in which the diluent, which may be a bottle of intravenous solution, is opened and the contents poured into a vial or bottle containing the dry or lyophilized material, have been commonly used. In, such cases, after reconstitution, the liquid is usually returned to the intravenous solution bottle or vial of other source of diluent. Techniques of this nature are unsatisfactory because of exposure to ambient airborne bacterial contamination.

Other proposals to enable reconstitution of medicaments or mixing of such materials have included the "intravenous set transfer" technique which requires an intravenous solution set and stand, and a needle for venting, or a special dispensing cap. Another approach has been to reconstitute using an ordinary syringe to transfer diluent into the container for the dry or lyophilized material. However, here again the needle is exposed to constant airborne contamination.

An improved technique for mixing medicaments of the type described has been disclosed in U.S. Pat. No. 3,882,909 to Robert W. Ogle. By this technique, described as "Trans-A-Jet-1", a fluid transfer device is provided which comprises two parallel fluid passages, both carried by a flange which is generally perpendicular to the passages. A common cover is provided for one end of each fluid passage which forms a fluid-tight seal with the exterior of the passage and abuts the flange. A medicament container having an open end and an imperforate stopper in the open end is provided.

Another device has been proposed in U.S. Pat. No. 3,857,392, issued to Robert W. Ogle, which comprises an intravenous container with a dislodgable septum and dislodging piercer. Mixing by dislodging an intervening septum is also proposed in a device described in U.S. Pat. No. 3,563,415, also issued to Robert W. Ogle.

The present invention is an improvement on the above-described mixing devices and techniques.

SUMMARY OF THE INVENTION

The present invention comprises a device suitable for mixing medicaments which comprises two separate containers. The first container is provided with a reservoir section and a neck section such that the cross section of the neck section is less than the cross section of the reservoir. A stopper is snugly fit within the neck section adjacent to the reservoir and a spike and plunger member is snugly fit within the neck section adjacent the stopper on the side opposite the reservoir. The spike and plunger member has a midportion with a hole therein, and a plunger projecting from the midportion adapted to make contact with the stopper. A spike extends from the midportion in the opposite direction.

In one embodiment of the invention a second container is provided which is adapted to snugly fit within the neck section adjacent the spike. The second container has a tiltable fluid-tight sealing means at one end thereof intended to be disposed adjacent the spike and an imperforate cap at the end thereof opposite the tiltable sealing means. The first container, stopper, spike and plunger member, and the second container, are arranged so that upon pressure applied to the second container, while the first container is restrained, the plunger dislodges the stopper and at the same time the spike tilts the sealing means of the second container so as to provide a communicating passageway between the second container and the reservoir in the first container via the hole in the midportion of the spike and plunger means member.

Advantageously, a removable external safety housing is provided which encompasses the second container and the neck portion of the first container and which extends at one end beyond the end of the second container having the imperforate cap dispose therein. By restraining the other end of the external housing, such as by resting the housing on the reservoir in a snug-fit manner, the housing thereby substantially prevents accidental contact with the imperforate cap end of the second container and the resulting accidental discharge and mixing of contents in the second and first containers that could thus occur.

It is also desirable to provide stop means in the neck section between the stopper and the midportion of the spike and plunger member so as to limit movement of the spike and plunger member in the direction of the reservoir. In this way, after the plunger dislodges the stopper, as for example, pushing it into the reservoir, further movement in that direction of the spike and plunger member would be prevented. The stop member also provides a resistance against which the mid portion of the spike and plunger member contacts so that spike will be able to engage the tiltable sealing means of the second container to break the fluid seal and thereby permit communication of the contents of the second container with the contents in the reservoir of the first container via the hole in the midportion of the spike and plunger member after the stopper has been dislodged.

In a second embodiment of the invention, the components of the device may be provided in a "kit" form. In this embodiment, one component comprises a first container as described above which includes a reservoir and neck portion, a stopper, and a spike and plunger member. Here again, the stopper provides a fluid seal for contents in the reservoir of the first container, but in this embodiment, a cap is provided at the other open end of the neck portion of the first container. The cap ensures the sterile condition of the contents within the first container while enabling storage thereof until needed.

The second component of the kit comprises the second container, as previously described, comprising a tiltable fluid-tight sealing means at one end and an imperforate cap at the other, but additionally includes an external housing extending from the imperforate cap end around the central body of the second container and beyond the end thereof having the tiltable sealing means. A closure cap is provided at the open end of the housing to protect the second container disposed therein.

When it is desired to effect mixing of the contents of the second container with the contents of the reservoir in the first container, the caps of the housing of the second container and the neck portion of the first container are removed and the central body of the second container is disposed within the neck portion of the first container so that the tiltable sealing means is located adjacent the spike of the spike and plunger member. Since the plunger of the spike and plunger member is disposed adjacent the stopper, the application of pressure at the imperforate cap end of the second container, while restraining the first container, thereby causes the plunger to dislodge the stopper in the first container and the spike to tilt the tiltable sealing means of the second container, and, once again, provide a continuous pathway for the contents of the second container to contact the contents in the reservoir of the first container via the hole in the midportion of the spike and plunger member. This second embodiment provides a convenient kit which may be stored until needed.

The invention, together with additional features and advantages thereof, may be best understood by reference to the following description taken in conjunction with the accompanying illustrative drawings.

DETAILED DESCRIPTION

Figure 1:
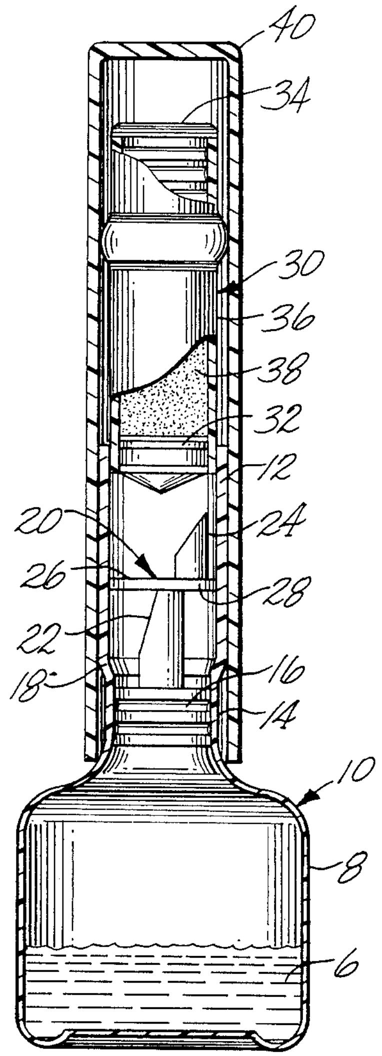
FIG. 1 is a side, partially sectional view, of one embodiment of the invention.

The mixing device shown in FIG. 1 generally comprises a first container 10, a stopper 16, a spike and plunger member 20, and a second container 30.

The first container 10 includes a reservoir section 8, in which maybe contained a liquid component 6 intended, for example, for use as a diluent, and a neck section 12. The neck section may advantageously include a portion 14 of reduced cross-sectional area in which the stopper 16 can be disposed.

The spike and plunger member 20 comprises a midportion 28, a plunger 22 extending from the midportion in the direction toward the reservoir, and a spike 24 extending from the midportion in the opposite direction. The midportion 28 also includes a hole or aperture 26 therewithin.

The second container 30 includes a central portion 36, tiltable fluid-tight sealing means 32, an and imperforate cap 34, at opposite ends of central body portion 36. The second container may contain a dry or powder contents 38 intended to be mixed with diluent 6. An external safety housing 40 may be provided to guard against accidental application of force to the second container 30 which would cause premature mixing of the contents 38 in the second container with the contents 6 in the first container. The safety housing 40 is constructed so as to have a cross-sectional area larger than the cross-sectional area of the neck section 12 of the first container 10, and to be of such a length as to be extendible beyond the imperforate cap end of the second container. The safety housing 40 may be restrained in any suitable manner against movement into contact with the second container, such as by resting snugly against the first container 10 in the embodiment shown in FIG. 1.

The mixing device containing the contents within the first and second containers ma be stored indefinitely until ready for mixing and use. When it is desired to effect mixing of the contents which, as previously indicated, may be any suitable medicaments which may be in a dry or lyophilized form, as indicated as 38 in the second container, and a liquid diluent such as indicated as 6 in the first container, external safety housing 40 is first removed. After removal of the housing, pressure may be applied to the imperforate cap end 34 of the second container while restraining the first container so as to cause the second container to slide within the neck section of the first container and make contact with the spike and plunger member 20. Continued pressure will cause the plunger to dislodge stopper 16 and push it into the reservoir while at the same time cause the spike 24 to tilt the tiltable sealing member 32 out of fluid-tight sealing engagement thereby providing a continuous pathway for the contents 38 of the second container to flow through the hole 26 in the midportion of the spike and plunger member into the reservoir 8 of the first container and thereby into contact with the contents 6 therein.

Mixing of the contents may be effected by agitating the device and the mixed contents can be withdrawn as necessary from the mixing device through the cap member 34 which may be adapted to receive a cannula or and I.V. connection.

Figure 2:
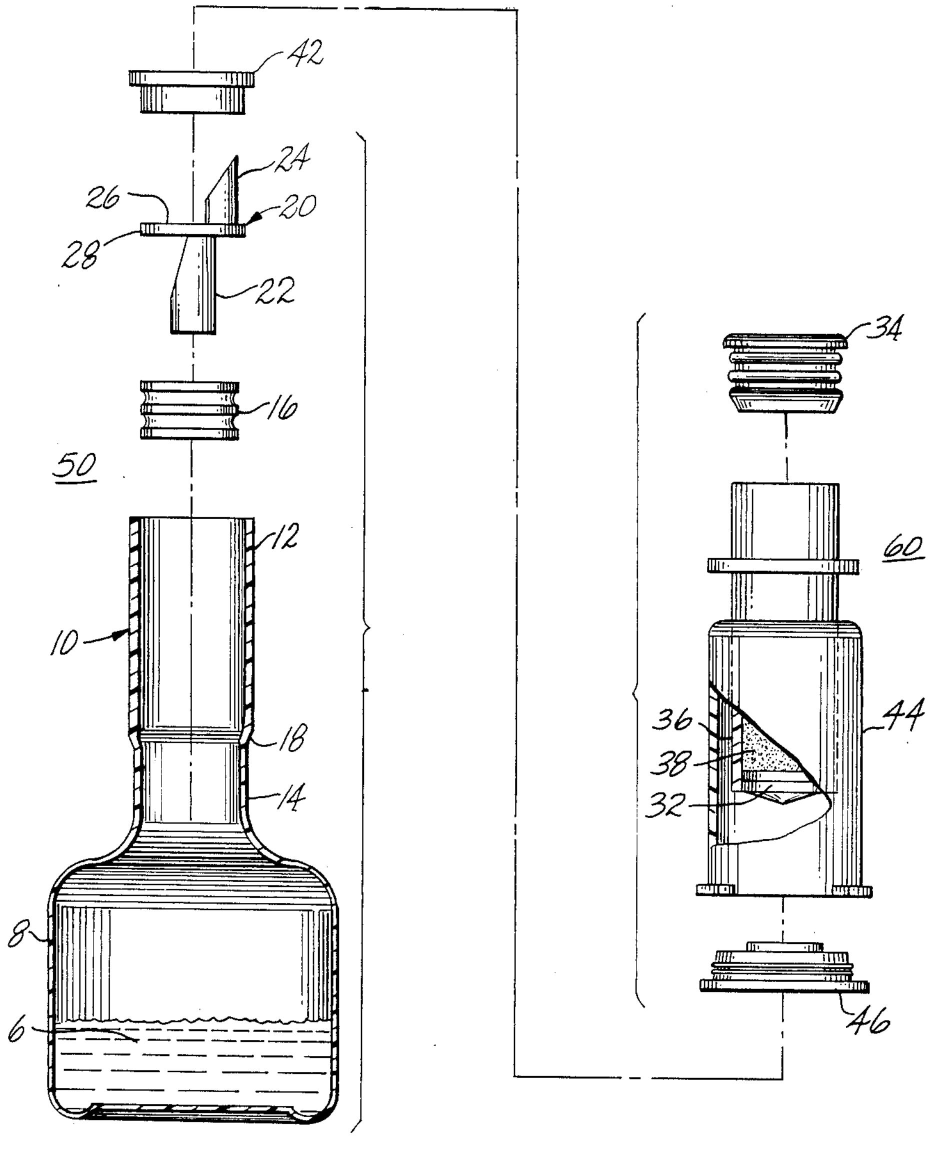
FIG. 2 is an exploded view, partially in section, of the second embodiment of the invention.

An alternative embodiment of the invention is shown in FIG. 2 in which the mixing device is provided as a "kit" comprising components 50 and 60 which constitute the first and second containers essentially as described in connection with FIG. In the FIG. 2 embodiment illustrated, like numerals refer to like or functionally equivalent components as illustrated and described in connection with FIG. 1.

As can be seen, one component of the kit comprises the first container 10 which includes a reservoir 8 and a neck section 12. Also included is a stopper 16 which is disposed within the neck section as shown in FIG. 1, and a spike and plunger member 20 disposed within the neck section adjacent the stopper, also as shown in FIG. 1. In this embodiment, however, a cap member 42 is provided to seal the open end of the neck section so that the first container constitutes an individual unit.

The second container is provided as a second separate unit 60 and comprises a central body portion 36 with tiltable fluid-sealing means 32 at one end, an imperforate cap 34 at the other end. However, in this embodiment, an external housing 44 is provided which extends from the imperforate cap end to beyond the tiltable sealing means 32. The extension beyond the seating means 32 is desirable to minimize or preclude contact therewith, thus preserving the sterile nature of the unit. In this arrangement, cap means 46 are also provided to seal the open end of the external housing 44 to also assist in maintaining the sterile condition. With the construction described in FIG. 2, the two components which form the kit may be stored indefinitely until it is desire to effect mixing of the contents 38 and 6 in the second and first containers, respectively.

When it is desired to use the kit, the caps 42 and 46 are removed from the first and second containers and the housing 44 is positioned around the neck portion 12 of the first container causing the second container to snugly but slidably fit within the neck portion with the tiltable sealing means 32 disposed adjacent the spike 24 of the spike and plunger member 20 located within the neck section of the first container. To effect mixing, pressure is applied to the imperforate cap end 34 of the second container until the plunger 22 dislodges the stopper 16 (into the reservoir 8) and the spike 24 tilts the tiltable sealing means 32 out of fluid-tight seal so as to permit the contents 36 of the second container to flow through the neck section via the hole 26 in the midportion 28 of the spike and plunger means.

A stop 18 shown in both FIG. 1 and FIG. 2 is provided to resist the further movement of the spike and plunger means toward the reservoir upon application of pressure to the imperforate cap end 34 of the second container, and to also permit sufficient resistance to enable the spike 24 to tilt the tiltable sealing means 32.

The invention has been described in accordance with the presently preferred embodiments. However, it is expressly understood that various changes and modifications may be made without departing from the scope of the invention, wherein:

What is claimed is:

1. A device suitable for mixing medicaments comprising:

a first container having a reservoir section and a neck section with a cross section less than the cross section of the reservoir;

a stopper snugly fit within the neck section adjacent the reservoir;

a spike and plunger member snugly fit within the neck section disposed adjacent the stopper on the side opposite the reservoir;

said spike and plunger member having a midportion with a hole therein, a plunger projecting from the midportion extending in the direction of the stopper and a spike extending from the midportion in the direction opposite the plunger;

a second container adapted to snugly fit within the neck section and deposed adjacent the spike;

said second container having a central body, tiltable sealing means at one end thereof disposed adjacent the spike and an imperforate cap at the end of the central body opposite the tiltable sealing means; and the first container, stopper, spike and plunger member and second container being arranged so that upon pressure applied to the second container while the first container is restrained, the plunger dislodges the stopper and the spike tilts the sealing means of the second container to provide a communicating path between the second container and the reservoir in the first container via the hole in the midportion of the spike and plunger member.

2. A device according to claim 1 further comprising stop means in the neck section between the stopper and the midportion of the spike and plunger member to limit movement thereof in the direction of the reservoir.

3. A device according to claim 1 wherein said imperforate cap of the second container is adapted to receive means to extract contents of said device after being mixed therein.

4. A device according to claim 1 further comprising a removable external safety housing encompassing the second container and neck portion of the first container which extends beyond and spaced from the sealing means of the second container and removably restrained at the opposite end, said housing thereby substantially preventing accidental contact with the imperforate cap end of the second container.

5. A kit suitable for mixing medicaments comprising:

a first container having a reservoir section and a neck section with a cross section less than the cross section of the reservoir;

a stopper snugly fit within the neck section adjacent the reservoir;

a spike and plunger member snugly fit within the neck section disposed adjacent the stopper on the side opposite the reservoir;

said spike and plunger member having a midportion with a hole therein, a plunger projecting from the midportion extending in the direction of the stopper and a spike extending from the midportion in the direction opposite the plunger;

a second container having a central body, a tiltable sealing means at one end thereof and an imperforate cap at the opposite end thereof;

a housing extending from the cap end around the central body, but spaced therefrom, to beyond the sealing means;

a removable housing closure cap at the end of the housing extending beyond the sealing means;

the cross section of the central body of the second container, the housing thereof and the neck section of the first container being such that upon removal of the housing closure cap and placement of the second container within the neck section with the tiltable sealing means disposed adjacent the spike of the spike and plunger member, the housing surrounds the neck portion and a portion of the central body of the second container snugly fits into the neck section;

the first container, stopper, spike member and second container being arranged so that upon pressure applied to the second container while the first container is restrained, the plunger of the spike member dislodges the stopper and the spike of the spike member tilts the sealing means of the second container, to provide a communication path between the second container and the reservoir in the first container via the hole in the midportion of the spike and plunger member, thereby enabling the contents of the first and second containers to make contact in the reservoir where they mix.

* * * * *

UNITED STATES PATENT AND TRADEMARK OFFICE
CERTIFICATE OF CORRECTION

PATENT NO. : 4,979,941
DATED : December 25, 1990
INVENTOR(S) : George B. Ogle, II It is certified that error appears in the above-identified patent and that said Letters Patent is hereby corrected as shown below:

Column 1, line 46, change "dislodgable" to -- dislodgeable --.

Column 2, line 19, change "dispose" to -- disposed --.
Column 2, line 35, change "mid portion" to -- midportion --.
Column 2, line 37, insert "the" before "spike".

Column 3, line 5, after "spike" delete "of the spike".
Column 3, line 34, change "maybe" to -- may be --.
Column 3, line 46, change "an and" to -- and an --.
Column 3, line 65, after "containers" change "ma" to -- may --.

Column 4, line 23, before "I.V." change "and" to -- an --.
Column 4, line 28, after "FIG." insert -- 1 --.
Column 4, line 54, change "desire" to -- desired --.

Column 5, line 1, after "contents" change "36" to -- 6 --.

UNITED STATES PATENT AND TRADEMARK OFFICE

CERTIFICATE OF CORRECTION

PATENT NO. : 4,979,941

DATED : December 25, 1990

INVENTOR(S) : George B. Ogle, II

It is certified that error appears in the above-identified patent and that said Letters Patent is hereby corrected as shown below:

Column 6, lines 38,39, after "spike" delete "of the spike".
Column 6, line 47, after "spike" delete "of the spike".

Signed and Sealed this

Twenty-eighth Day of July, 1992

*Attest:*

DOUGLAS B. COMER

*Attesting Officer*

*Acting Commissioner of Patents and Trademarks*